US006810595B2

(12) United States Patent
Chan

(10) Patent No.: US 6,810,595 B2
(45) Date of Patent: Nov. 2, 2004

(54) LASER ANGLE GUIDE ASSEMBLY FOR COMPUTED TOMOGRAPHY AND METHOD FOR THE SAME

(76) Inventor: Wing-Sheung Chan, 5F, No. 10, Lane 47, Yuying St., Taiping City, Taichung Hsien (TW)

( * ) Notice: Subject to any disclaimer, the term of this patent is extended or adjusted under 35 U.S.C. 154(b) by 0 days.

(21) Appl. No.: 10/327,011

(22) Filed: Dec. 24, 2002

(65) Prior Publication Data

US 2004/0117996 A1 Jun. 24, 2004

(51) Int. Cl.[7] .......................... A61B 19/00; G01C 15/00; G01B 11/26
(52) U.S. Cl. .............................. 33/286; 33/283; 33/512; 33/DIG. 21; 606/130
(58) Field of Search .......................... 33/DIG. 21, 227, 33/228, 263, 282, 283, 286, 512, DIG. 1; 605/130; 600/429, 425, 426

(56) References Cited

U.S. PATENT DOCUMENTS

| | | | | |
|---|---|---|---|---|
| 4,669,195 A | * | 6/1987 | Griffin ........................... | 33/339 |
| 4,699,186 A | * | 10/1987 | Palin et al. ..................... | 141/2 |
| 4,722,336 A | * | 2/1988 | Kim et al. ................... | 606/130 |
| 4,733,661 A | * | 3/1988 | Palestrant ..................... | 606/108 |
| 4,841,967 A | * | 6/1989 | Chang et al. ................ | 606/130 |
| 5,102,391 A | * | 4/1992 | Palestrant .................... | 604/116 |
| 5,246,448 A | * | 9/1993 | Chang ......................... | 606/130 |
| 5,308,352 A | * | 5/1994 | Koutrouvelis ................ | 606/130 |
| 5,419,050 A | * | 5/1995 | Moore .......................... | 42/115 |
| 5,450,909 A | * | 9/1995 | Stevenson .................... | 172/430 |
| 5,575,798 A | * | 11/1996 | Koutrouvelis ................ | 606/130 |
| 5,598,269 A | * | 1/1997 | Kitaevich et al. ............ | 356/399 |
| 5,782,842 A | * | 7/1998 | Kloess et al. ................ | 606/130 |
| 5,810,841 A | * | 9/1998 | McNeirney et al. ......... | 606/130 |
| 5,836,081 A | * | 11/1998 | Orosz, Jr. ..................... | 33/290 |
| 6,021,342 A | * | 2/2000 | Brabrand ..................... | 600/427 |
| 6,044,291 A | * | 3/2000 | Rockseisen .................. | 600/429 |
| 6,351,890 B1 | * | 3/2002 | Williams ...................... | 33/286 |
| 6,470,578 B1 | * | 10/2002 | Phuly et al. ................... | 33/286 |
| 6,605,095 B2 | * | 8/2003 | Grossman .................... | 606/130 |
| 6,640,453 B2 | * | 11/2003 | Eisenmenger ................ | 33/283 |

* cited by examiner

*Primary Examiner*—Diego Gutierrez
*Assistant Examiner*—R. Alexander Smith
(74) *Attorney, Agent, or Firm*—Rosenberg, Klein & Lee

(57) ABSTRACT

A laser angle guide assembly has a stand and a laser guide. The laser guide is rotatably attached to the stand and has a laser pointer, a transparent column, a guiding rod, an index stick and a protractor. The laser pointer has a head for emitting a laser. The transparent column is attached to the laser pointer to transfer the laser to an index line with an inclination. The guiding bar is attached to the laser pointer. The index stick is attached to the guiding bar and has an index section with an inclination parallel to the inclination of the index line. The protractor with graduations is rotatably attached to the index stick and corresponds to the index section. Accordingly, the laser pointer will generate an index line to provide a guide to the doctor to insert the needle into the patient body at a desired angle.

9 Claims, 6 Drawing Sheets

US 6,810,595 B2

LASER ANGLE GUIDE ASSEMBLY FOR COMPUTED TOMOGRAPHY AND METHOD FOR THE SAME

BACKGROUND OF THE INVENTION

1. Field of the Invention

The present invention relates to a laser angle guide assembly, and more particularly to a laser angle guide assembly for computed tomography (CT) and a method for the same.

2. Description of Related Art

Computed tomography is a conventional way to scan a patient for biopsy, and a specimen of tissue will be removed from the patient and be examined by a pathologist to check diseases, such as cancer. With reference to FIGS. 5 and 6, a computed tomograph (80) and a puncturing needle assembly (70) are used to remove a specimen of tissue from a patient. The computed tomograph (80) has multiple scanners (83) arranged around a patient who lies on a bed (81) and is held by a holder (82), such as a vacuum immobilization mat. A doctor will remove a specimen of tissue from the patient with the puncturing needle assembly (70) at a desired position, angle and depth determined by the computed tomograph (80). The puncturing needle assembly (70) has a needle (72) for puncturing into the body (90) of the patient to take the specimen out from the body (90). A positioning guide, such as a pin or a paper soaked with developer is put on the desired puncturing position on the body (90) of the patient to help the doctor to puncture at a desired position. Graduations are marked on the needle (72) to help the doctor to check the puncturing depth.

However, there is no guide for the puncturing angle during the specimen process. The angle for the needle (72) puncturing into the body (90) is dependent on the experience and the intuition of the doctor. If the puncturing angle has a large deviation relative to the desired puncturing angle, this will cause pain to the patient and even to lead complications to the patient.

To overcome the shortcomings, the present invention tends to provide a laser angle guide assembly and a method for the same to mitigate or obviate the aforementioned problems.

SUMMARY OF THE INVENTION

The main objective of the invention is to provide a laser angle guide assembly that can generate an index line to help a doctor to puncture at a desired angle. The laser angle guide assembly has a stand and a laser guide. The laser guide is rotatably attached to the stand and has a laser pointer, a transparent column, a guiding rod, an index stick and a protractor. The laser pointer is rotatably attached to the stand and has a head for emitting a laser. The transparent column is attached to the head of the laser pointer to transfer the laser emitted from the head to an index line with an inclination. The guiding bar is attached to the laser pointer. The index stick is attached to one end of the guiding bar and has an index section with an inclination parallel to the inclination of the index line. The protractor with graduations is rotatably attached to the free end of the index stick and corresponds to the index section. Accordingly, the laser pointer will generate an index line with the transparent column, and the inclination of the index can be read from the graduation on the protractor. The index line can provide a guide to the doctor to insert the needle into the patient body at a desired angle.

Other objects, advantages and novel features of the invention will become more apparent from the following detailed description when taken in conjunction with the accompanying drawings.

DETAILED DESCRIPTION OF PREFERRED EMBODIMENT

Figure 1:
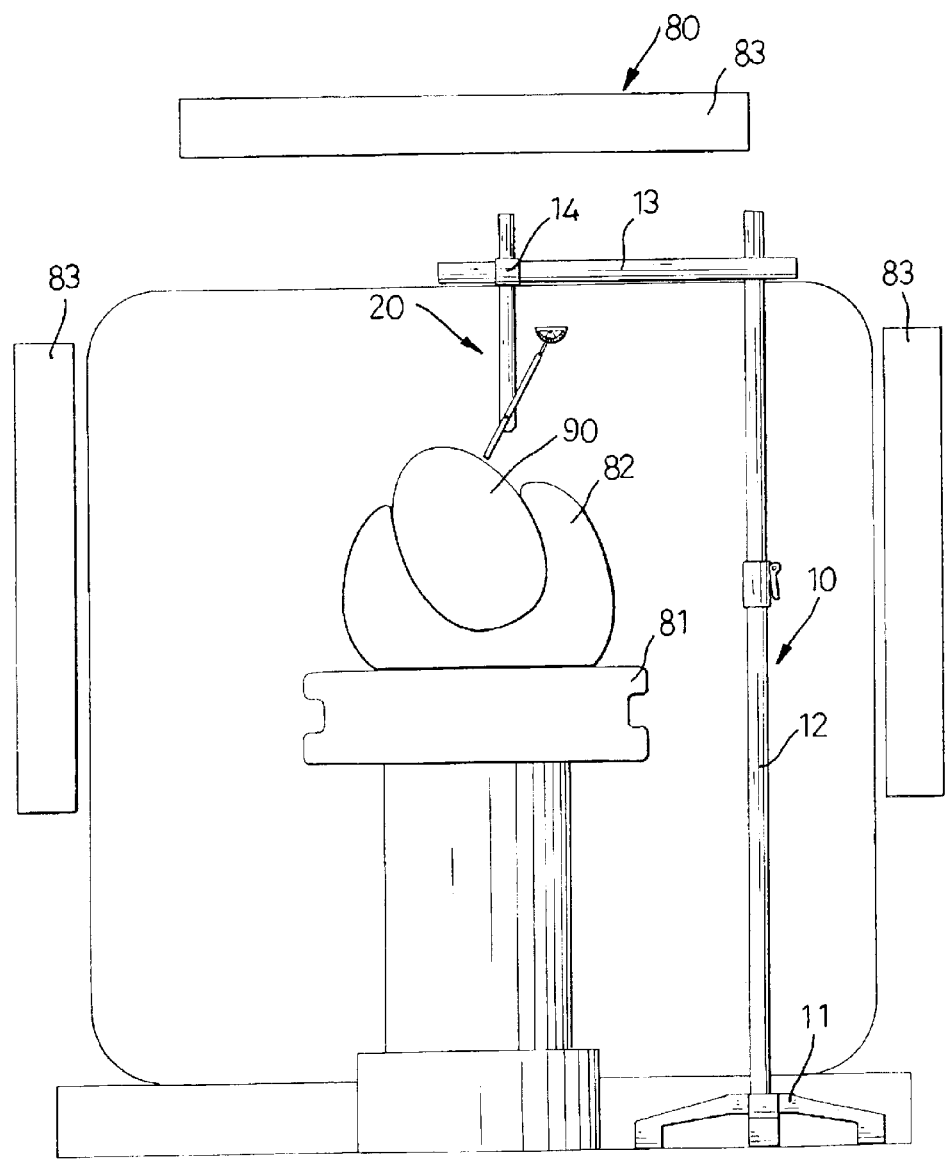
FIG. 1 is a side plan view of a computed tomograph with a laser angle guide assembly in accordance with the present invention.
Figure 2:
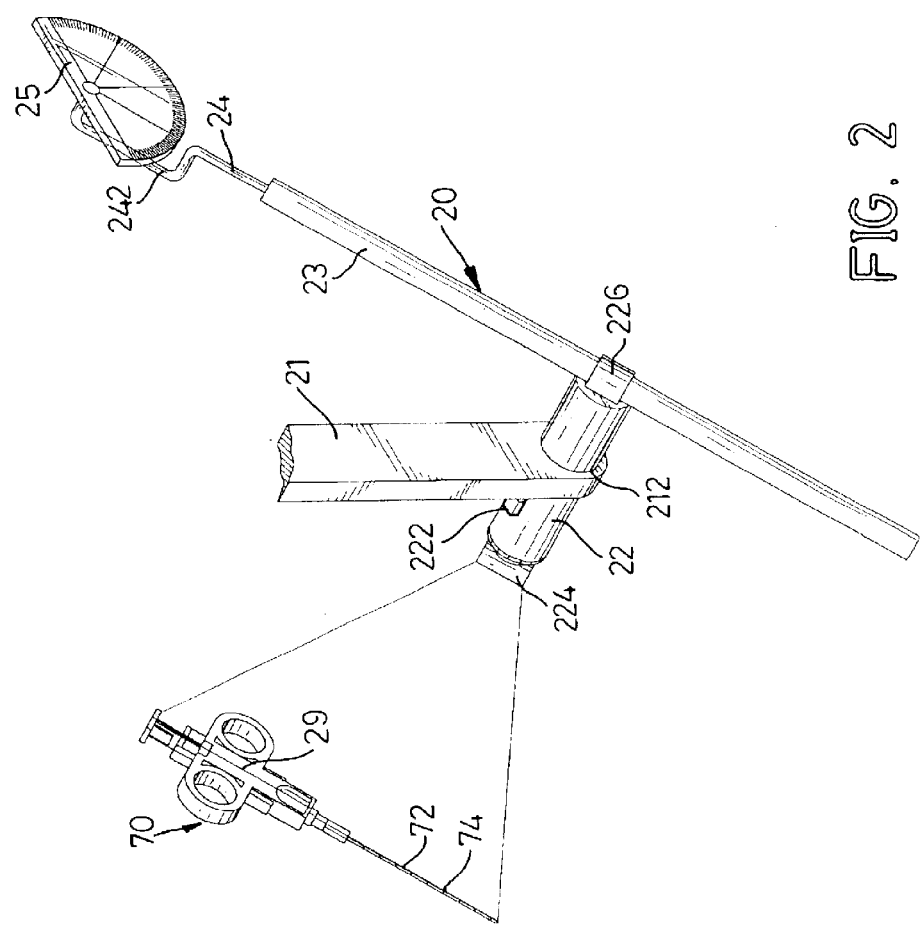
FIG. 2 is an operational perspective view of a puncturing needle assembly with the laser guide of the laser angle guide assembly in FIG. 1.

With reference to FIGS. 1 and 2, a laser angle guide assembly for a puncturing process with computed tomography (CT) in accordance with the present invention comprises a stand (10) and a laser guide (20). The stand (10) comprises a base (11), a post (12), a lateral rod (13) and an arm (21). The post (12) extends upward from the base (11). The lateral rod (13) is laterally mounted near the top end of the post (12). The arm (21) is moveably mounted on the lateral rod (13) and has a through hole (212), and the laser guide (20) is mounted in the through hole (212) in the arm (21). In practice, an annular connector (14) is mounted around the lateral rod (13), and the arm (21) is securely attached to the connector (14). Consequently, the arm (21) is moveably mounted on the lateral rod (13), and the position of the laser guide (20) is adjustable. In addition, the post (12) can be designed to be telescopic, such that the height of the laser guide (20) can also be adjusted.

The laser guide (20) is rotatably attached to the arm (21) of the stand (10). The laser guide (20) has a laser pointer (22), a transparent column (224), a guiding bar (23), an index stick (24) and a protractor (25). The laser pointer (22) is rotatably received in the through hole (212) in the arm (21) and has a head for emitting a laser. A switch (222) is mounted on the laser pointer (22) to control the operation of the laser pointer (22). The transparent column (224) is attached to the head of the laser point (22) to transfer the laser emitted from the head to an index line (29) with an inclination. In practice, the transparent column (224) has an axis perpendicular to the direction of the emitted laser from the head of the laser pointer (22). Accordingly, the index line (29) will be generated by means of the refraction effect of the transparent column (224) when the laser passes through the transparent column (224).

A collar (226) is attached to the laser pointer (22) at the end far from the head. The guiding bar (23) extends through the collar (226) and is attached to the laser pointer (22)

through the collar (226). The guiding bar (23) has an inclination parallel to the inclination of the index line (29). The index stick (24) is attached to one end of the guiding bar (23) and has an index section (242) with an inclination parallel to the inclination of the index line (29). The protractor (25) is rotatably attached to the free end of the index stick (24). The protractor (25) is semicircular and has an arcuate edge and a central point serving as a center of the arcuate edge. The protractor (25) is rotatably attached to the free end of the index stick (24). The protractor (25) has a graduation (252) arranged around the arcuate edge and corresponding to the index section (242) of the index stick (24). Accordingly, the protractor (25) will automatically keep in a horizontal level due to the weight of the protractor (25) even when the guiding bar (23) is rotated relative to the arm (21). The inclination of the index section (242) can be read from the graduation (252) on the protractor (25). Because the inclination of the index section (242) is parallel to the inclination of the index line, the inclination of the index line can also be read from the protractor (25).

Figure 3:
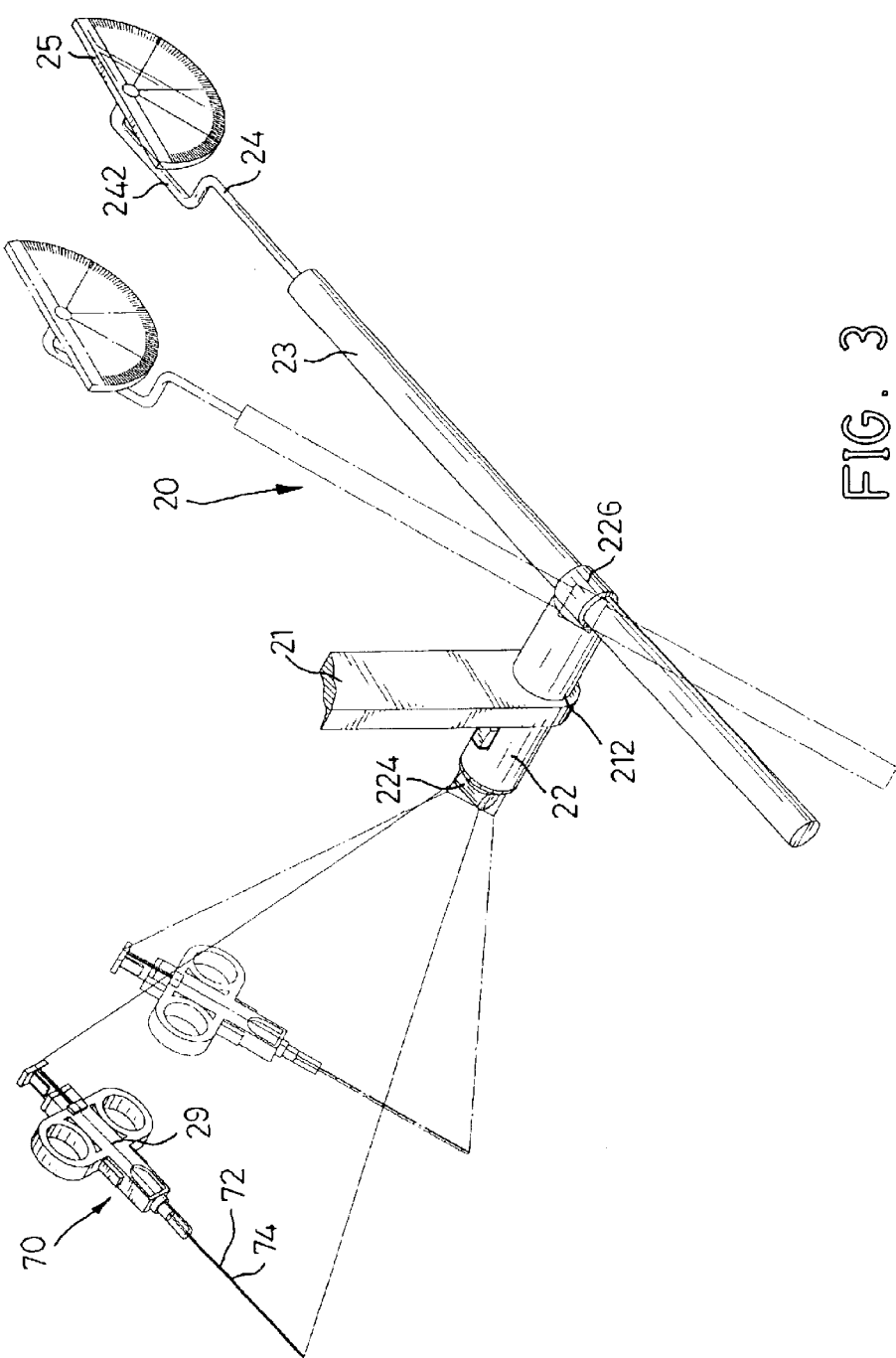
FIG. 3 is an operational perspective view of the puncturing needle assembly with the laser guide in FIG. 2 showing that the puncturing angle of the puncturing needle assembly is adjusted according to the index line emitted from the laser guide.

With reference to FIGS. 1 to 3, when the patient lies on the bed (81) and is held by a holder (82), the computed tomograph (83) will scan the patient with the scanners (83) for biopsy to determine the desired puncturing position, angle and depth for the biopsy. The laser guide (20) is moved to a desired position by means of adjusting the post (12) and moving the arm (21) relative to the lateral rod (13). The laser pointer (22) is then switched on, and the index line (29) will be generated through the transparent column (224). The guiding bar (23) is rotated to a position where the index section (242) of the index stick (24) has an inclination parallel to the desired puncturing angle calculated by the computed tomograph (80). Because the guiding bar (23) is connected to the laser pointer (22), the laser pointer (22) will be rotated with the guiding bar (23). Consequently, the inclination of the index line (29) will be adjusted by means of rotating the guiding bar (23). Accordingly, the doctor can precisely insert the needle (72) of the puncturing needle assembly (70) into the body (90) at a desired angle, and this can keep the patient from pain and complications. In addition, the puncturing depth can be checked from the gradations (74) marked on the needle (72).

Figure 4:
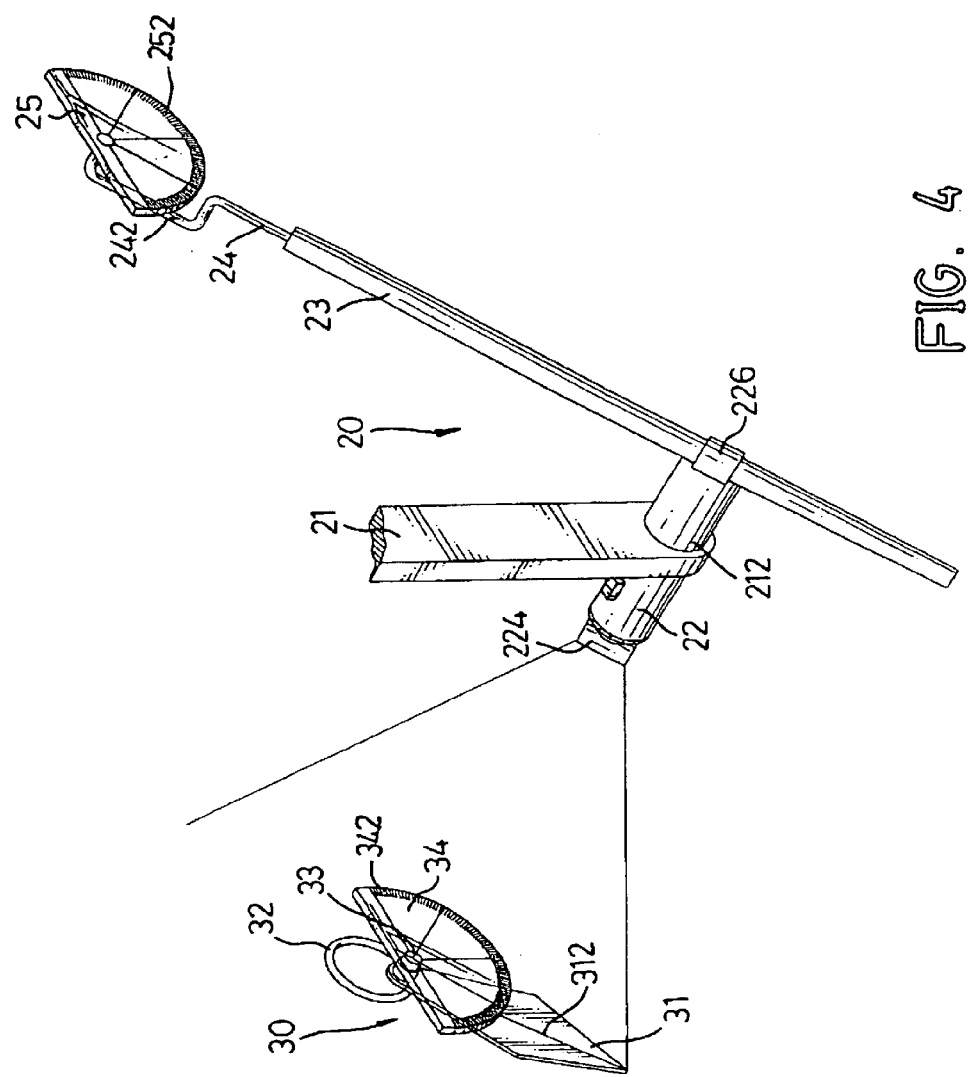
FIG. 4 is an operational perspective view of a laser guide with a rectifying device in accordance with the present invention.
Figure 5:
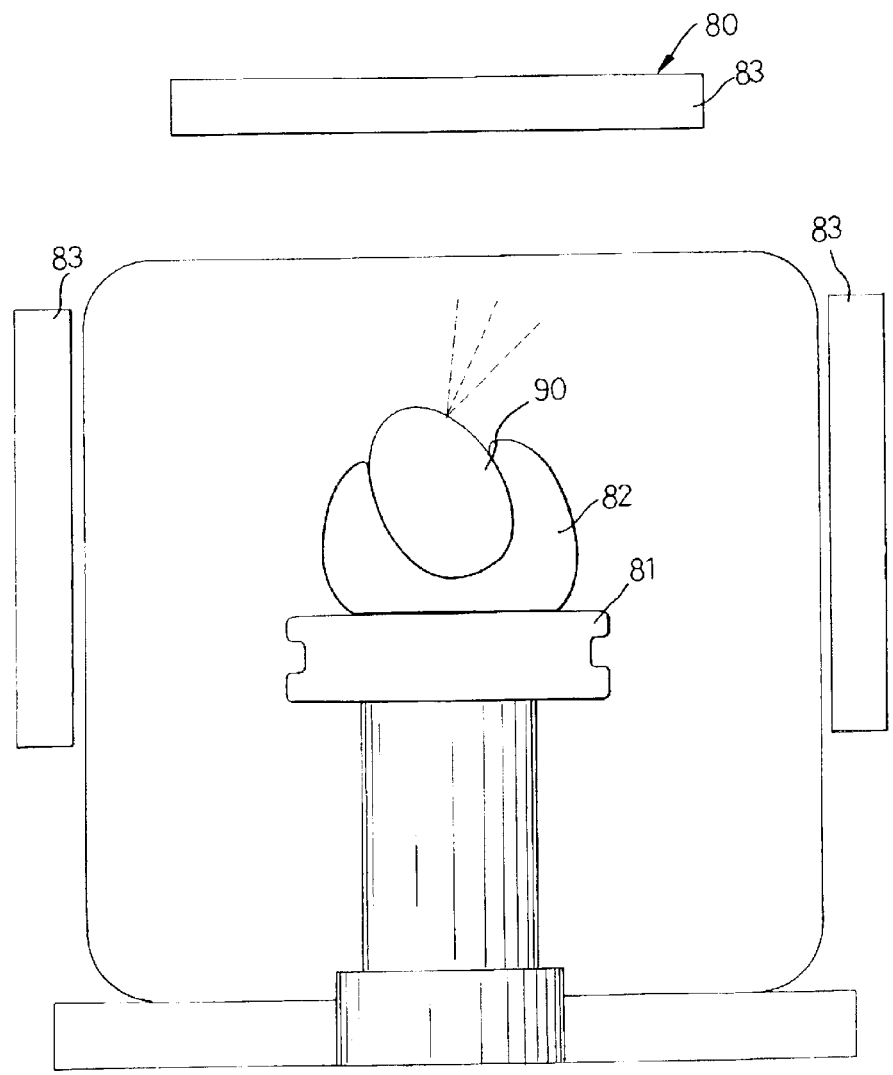
FIG. 5 is a side plan view of a conventional puncturing process with a computer tomograph in accordance with the prior art.
Figure 6:
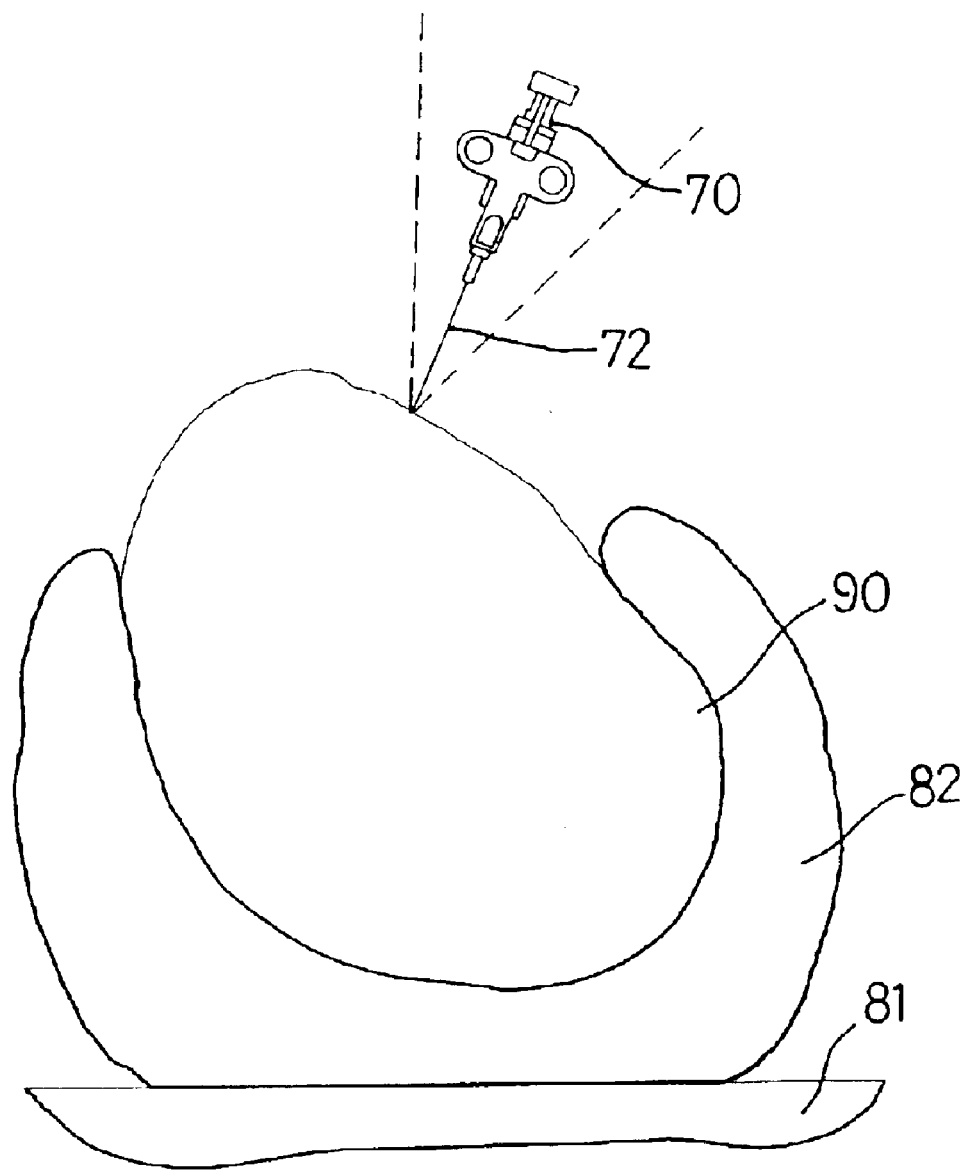
FIG. 6 is an operational side plan view of a conventional puncturing process with a puncturing needle assembly in accordance with the prior art.

With reference to FIG. 4 in accordance with FIG. 2, the laser angle guide assembly further comprises a rectifying device (30) to rectify the accuracy of the laser guide (20). The rectifying device (30) comprises an index plate (31) and a rectifying plate (34). The index plate (31) corresponds to the index line (29) emitted from the laser pointer (22) and has a rectifying line (312). The rectifying plate (34) is semicircular and has an arcuate edge and a central point serving as the center of the arcuate edge. The rectifying plate (34) is rotatably attached to an axle (33) mounted on the index plate (34) at the central point, such that the rectifying plate (34) will automatically keep in a horizontal level due to the weight of the rectifying plate (34). The rectifying plate (34) has a graduation (342) marked around the arcuate edge and corresponding to the rectifying line (312) on the index plate (31).

To rectify the inclination of the index line (29) emitted from the laser pointer (22), the user holds the index plate (31) to align the rectifying line (312) with the index line (29). Accordingly, the inclination of the index line (29) can be read from the graduation (342) on the rectifying plate (34), and the inclination of the index line (29) can be rectified by means of rotating the guiding bar (23) according to the graduation on the rectifying plate (34). In addition, a ring (32) is attached to the index plate (31) for a user to conveniently hold the rectifying device (30).

Even though numerous characteristics and advantages of the present invention have been set forth in the foregoing description, together with details of the structure and function of the invention, the disclosure is illustrative only, and changes may be made in detail, especially in matters of shape, size, and arrangement of parts within the principles of the invention to the full extent indicated by the broad general meaning of the terms in which the appended claims are expressed.

What is claimed is:

1. A laser angle guide assembly for a puncturing process with computed tomography comprising:
    a stand;
    a laser guide rotatably attached to the stand and comprising:
        a laser pointer rotatably attached to the stand and having a head for emitting a laser;
        a transparent column attached to the head of the laser pointer to transfer the laser emitted from the head to an index line with an inclination;
        a guiding bar attached to the laser pointer;
        an index stick attached to one end of the guiding bar and having an index section with an inclination parallel to the inclination of the index line and a free end; and
        a protractor with a graduation rotatably attached to the free end of the index stick and corresponding to the index section, said protractor maintaining a horizontal level by virtue of its own weight.

2. The laser angle guide assembly as claimed in claim 1, wherein the stand comprises:
    a base;
    a post extending upward from the base and having a top end;
    a lateral rod laterally mounted near the top end of the post; and
    an arm moveably mounted on the lateral rod and having a through hole defined in the arm for the laser pointer being rotatably received in the through hole.

3. The laser angle guide assembly as claimed in claim 1, wherein the guiding bar has an inclination parallel to the inclination of the index line.

4. The laser angle guide assembly as claimed in claim 1, wherein the protractor is semicircular and has an arcuate edge and a central point serving as a center or the actuate edge, and the protractor is attached to the free end of the index stick; and
    the graduation is marked around the arcuate edge of the protractor.

5. The laser angle guide assembly as claimed in claim 1 further comprising a rectifying device corresponding to the transparent column and the index line and having:
    an index plate with a rectifying line corresponding to the index line; and
    a rectifying plate pivotally attached to the index plate and having a graduation corresponding to the rectifying line and the index line, said rectifying plate maintaining a horizontal level by virtue of its own weight.

6. The laser angle guide assembly as claimed in claim 5, wherein the rectifying device further comprises a ring attached to the index plate and adapted for a user to hold the rectifying device.

7. The laser angle guide assembly as claimed in claim 5, wherein the index plate has an axle for the rectifying plate to be pivotally attached to the axle.

8. The laser angle guide assembly as claimed in claim 7, wherein the rectifying plate is semicircular and has an arcuate edge and a central point served as a center of the actuate edge and attached to the axis; and the graduation on the rectifying plate is marked on the arcuate edge.

9. The laser angle guide assembly as claimed in claim 1 further comprising a switch mounted on the laser pointer.

* * * * *